United States Patent [19]
Bouraly et al.

[11] Patent Number: 5,490,855
[45] Date of Patent: Feb. 13, 1996

[54] DEVICE TO STABILZE A CUTTING MEANS FOR THE FITTING OF A PROSTHESIS IN BONE SURGERY

[75] Inventors: Jean-Pierre Bouraly, Montbeliard; Jurg Aebi, Rodez; Philippe Beaufils, Magny les Hameaux; Michel de Lestang, Amiens; Jean-Gilles Gaffuri, Rumilly En Cambresis; Hervé Hourlier, Wignehies; Jean-Jacques Lallement, St. Andre Les Vergers; Philippe Legroux, Le Bouscat; Jean-Paul Levai, Clermond-Ferrand; Gérald Pondaven, Quimper; Pierre Schuster, Saint Avold; Christian Vergnat, Metz, all of France

[73] Assignees: Developpement D'Implants Orthopediques et Medicaux; Protek Synthes, both of Etupes Cedex, France

[21] Appl. No.: 187,260

[22] Filed: Jan. 27, 1994

[51] Int. Cl.⁶ .................................... A61B 17/56
[52] U.S. Cl. ................... 606/88; 606/87; 606/82
[58] Field of Search ................... 606/88, 87, 89, 606/86, 95, 96, 98, 82, 62, 65

[56] References Cited

U.S. PATENT DOCUMENTS

| | | | |
|---|---|---|---|
| 2,696,817 | 12/1954 | Prevo | 606/62 |
| 3,118,444 | 1/1964 | Serrato, Jr. | 606/62 |
| 4,474,177 | 10/1984 | Whiteside | 606/88 |
| 4,487,203 | 12/1984 | Androphy | 606/88 |
| 4,887,310 | 12/1989 | Meyzonnette et al. | |
| 4,927,422 | 5/1990 | Englehardt | |
| 5,002,545 | 3/1991 | Whiteside et al. | |
| 5,037,423 | 8/1991 | Kenna | 606/88 |
| 5,053,037 | 10/1991 | Lackey | |
| 5,129,909 | 7/1992 | Sutherland | 606/88 |
| 5,180,382 | 1/1993 | Frigg et al. | |
| 5,234,433 | 8/1993 | Bert et al. | 606/88 |
| 5,342,367 | 8/1994 | Ferrante et al. | 606/86 |
| 5,342,368 | 8/1994 | Petersen | 606/88 |

FOREIGN PATENT DOCUMENTS

| | | |
|---|---|---|
| WO91/19461 | 12/1991 | WIPO . |
| 9203979 | 3/1992 | WIPO ............ 606/62 |

*Primary Examiner*—Stephen C. Pellegrino
*Assistant Examiner*—Guy V. Tucker
*Attorney, Agent, or Firm*—Pollock, Vande Sande & Priddy

[57] ABSTRACT

A device for the axial stabilization of a cutting means, used to make at least one cut at one end of a bone with a view to the fitting of a prosthesis in bone surgery. It includes an axial centering rod that is introduced partially into the intramedullar canal of said bone and is designed to receive said one cutting means. The centering rod is provided with an anchoring thread so as to form a anchor bolt that is axially stabilized in a direction parallel to the axis of the rod. A clamping device is mounted to the rod and axially clamps the cutting means inst the bone.

3 Claims, 1 Drawing Sheet

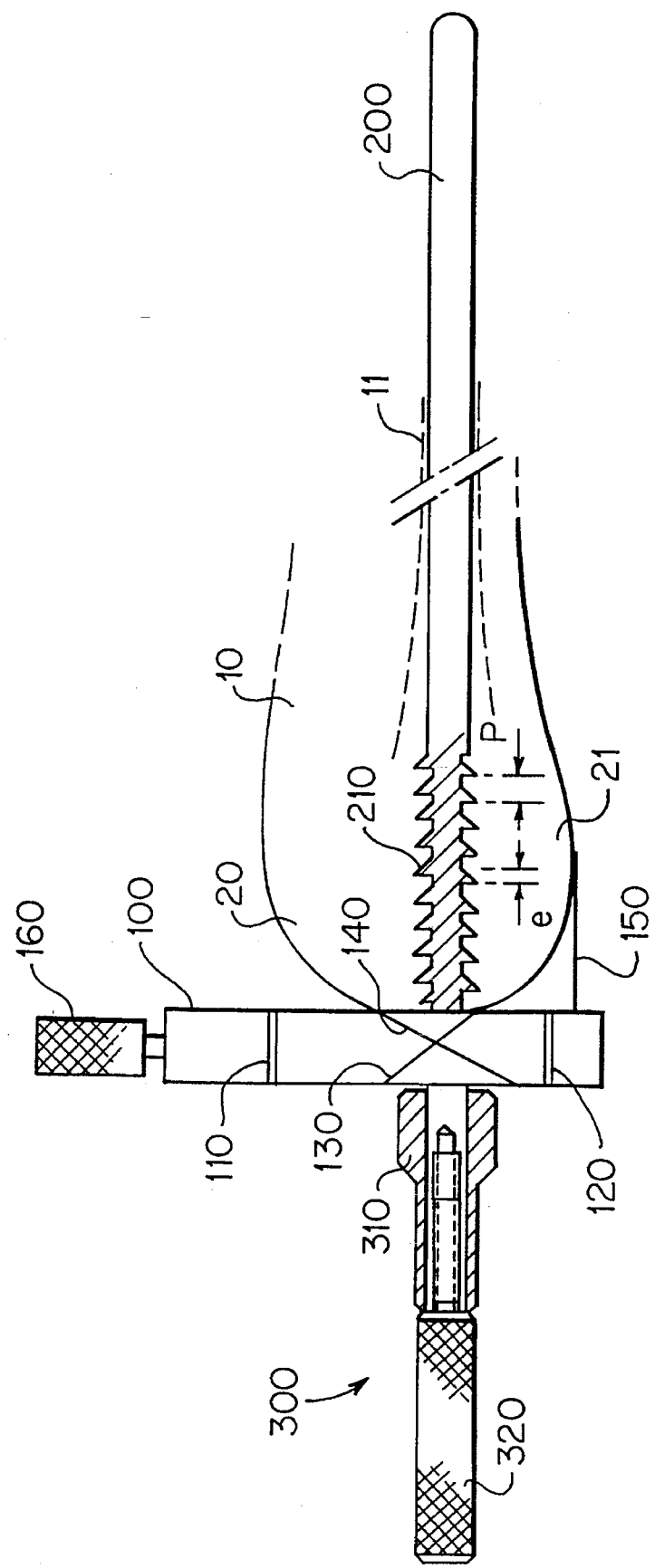

DEVICE TO STABILZE A CUTTING MEANS FOR THE FITTING OF A PROSTHESIS IN BONE SURGERY

BACKGROUND OF THE INVENTION

1. Field of the Invention

The present invention relates to a device for the axial stabilization of a cutting means used to carry out at least one cutting operation at an end of a bone in order to fit a prosthesis in bone surgery.

The invention can be applied in a particularly advantageous way, but not exclusively, to the fitting of knee replacements.

2. Description of the Prior Art

In general, the fitting of a prosthesis in bone surgery requires the use of a tool outfit, called a set of ancillary equipment, that makes it possible to prepare the fitting of the prosthesis itself. In the case of a femoral prosthesis of the knee, having a certain number of planar, internal contact surfaces, corresponding cuts have to be made at the distal end of the femur so as to ensure the perfect positioning of the prosthesis on the bone thus prepared. To this end, a cutting means, such as a multiple-cutting block or guide, is used, and this means must be kept in a stable position at the distal end of the femur. One technique that is used, described in the U.S. Pat. No. 5,129,909, consists in fixing said multiple-cutting block or guide against the end of the femur by means of two screws that are directly implanted in the bone symmetrically with respect to the intramedullar canal. However, this known method has many drawbacks. First of all, it calls for a prior identification of the orientation of the block or guide in order to define a fixed geometrical reference for the subsequent cuts. Furthermore, the screwing and unscrewing of the fastening screws cause unnecessary bone damage.

Hence, the technical problem to be resolved by the object of the present invention is to propose a device for the axial stabilization of a cutting means used to make at least one cut at one end of a bone with a view to the fitting of a prosthesis in bone surgery, said device making it possible to obtain perfect stability of the cutting means in the axial direction while, at the same time, providing for the positioning and removal of said cutting means without damage to the bone tissues and without any prior identification of orientation.

SUMMARY OF THE INVENTION

According to the present invention, there is proposed a solution to the present problem wherein said device comprises a centering rod that is introduced partially into the intramedullar canal of said bone and is designed to receive said cutting means, said centering rod being provided with an anchoring thread so as to form an anchor bolt that is axially stabilized in a direction parallel to the axis of the rod.

Thus, the anchoring thread with which the rod is provided ensures perfect axial stability of the cutting means and the rod forming an anchor bolt can be extracted very easily by the unscrewing of the rod, without any bone damage being caused by this operation. Furthermore, the intramedullar canal in itself constitutes a natural geometrical reference: this means that the practitioner is spared the need to make unnecessary movements to identify the orientation, which is essential in cases of sepsis.

Naturally, the device according to the invention may be implemented with all types of cutting means, whether these are single-cut guides placed successively on the same anchor bolt or again just one block that can be used to make all the cuts required.

The latter cutting means is particularly advantageous since it ensures ideal correlation of the successive cuts. To obtain a perfect result, it suffices to keep the cutting means in a determined axial position. To this end it is provided, according to the invention, that said device will comprise also means to clamp said cutting means against the end of the bone. The cutting means, in being thus kept permanently in a clamped position against the bone, constitutes a fixed geometrical reference to make the successive cuts.

BRIEF DESCRIPTION OF THE DRAWING

The following description, made with reference to the appended drawing and given by way of a non-restrictive example, will give a clear understanding of what the invention consists of and the way in which it can be made.

FIG. 1 shows a sectional view of a tool outfit for the fitting of a femoral prosthesis of the knee, comprising a longitudinal stabilization device according to the invention.

MORE DETAILED DESCRIPTION

FIG. 1 shows a sectional view of a tool outfit, also called a set of ancillary equipment, for the fitting of a femoral prosthesis of the knee. This ancillary equipment comprises a cutting means 100 which, in the sectional view shown in FIG. 1, is a block that can be used to make a plurality of cuts at the end 20 of a bone 10, in this case the femur, by means of slots 110, 120, 130, 140 through which an oscillating saw (not shown) is placed successively. It will be noted that the femur cutting block 100 has posterior lugs 150 that are placed so as to lean against the posterior condyles of the femur 10 by the activation of a anterior/posterior setting knob screw 160.

As can be seen in FIG. 1, the fitting ancillary equipment comprises a device for the axial stabilization of the block 100, comprising a centering intramedullar rod 200 introduced partially into the intramedullar canal 11 of the femur 10 and designed to receive the femur cutting block 100.

In accordance with FIG. 1, the rod 200 is provided with an anchoring thread 210, thus forming an anchor bolt that is axially stabilized in a direction parallel to the axis of the rod 200.

The block 100 is therefore perfectly centered with respect to the axis of the femur 10 and, to stabilize it in the axial direction, it is enough to join it fixedly to the rod 200 forming an anchor bolt. To this end, the device shown in FIG. 1 also comprises a means 300 to apply and compress the femoral cutting block 100 against the end 20 of the bone 10.

As can be seen in FIG. 1, said applying and clamping means 300 is constituted by a knob screw 320 that is mounted at the proximal end of the anchor bolt 200 and drives a shoulder 310 designed to take clamp the cutting block 100 against the bone 10.

It can be seen in FIG. 1 that said anchoring thread 210 is made in the proximal part of the rod 200 forming an anchor bolt, the distal length of the rod acting as a guiding means through the intramedullar canal.

In practice, the length of the thread ranges from 10% to 50% of the anchor bolt 200. Owing to its limited length, it is preferable to provide for a thread shape that can give an anchoring volume capable of immobilizing the rod 200 axially in the bone 10. To this end, there is proposed a thread with a thickness e that is smaller than the pitch p, the ratio e/p being at most equal to 25%. Thus, the thread made has a very fine edge with a space capable of housing sufficient bone stock, given the fact that the medium into which the anchor bolt 200 is inserted has relatively little resistance.

The applicants have established the fact that a sound compromise between sufficient anchoring volume and a thread with a diameter compatible with the dimensional characteristics of the bone is obtained when the ratio of the diameter of the thread 210 to the diameter of the rod 200 is in the 1.5 to 1.8 range.

The threading is done, for example, by the machining of a rod made of thermally hardened austenitic steel.

What is claimed is:

1. An axially stabilized apparatus used for cutting the end of a bone in preparation of fitting a prosthesis during bone surgery, comprising: a removable centering rod for partial insertion into an intramedullar canal of the bone;

a first threaded portion formed only on an intermediate section of the rod for threaded anchoring engagement with a proximal end of the bone canal, that axially stabilizes the rod;

a cutting block slidably mounted to an axial external intermediate extension of the centering rod, at a point outwardly adjacent a proximal end of the bone; and threaded fastener means mounted on an outward axial end portion of the centering rod, having a second threaded portion for exerting a clamping force, axial with the rod, to clamp the block against the bone.

2. The apparatus set forth in claim 1 wherein the ratio of the thread thickness of the threaded portion, to its pitch, is less than 25%.

3. An axially stabilized apparatus used for cutting the end of a bone in preparation of fitting a prosthesis during bone surgery, comprising:

a centering rod for partial insertion into an intramedullar canal of the bone;

a threaded portion formed on an intermediate section of the rod for threaded anchoring engagement with a proximal end of the bone canal, that axially stabilizes the rod;

a cutting block slidably mounted to the centering rod, at a point outwardly adjacent a proximal end of the bone; and means mounted on an outward end portion of the centering rod for axially clamping the block against the bone;

wherein the threaded rod portion has a length less than 50% of the overall rod length, and sufficient diameter to secure the centering rod axially immobilized in the bone.

* * * * *